United States Patent
Pearl et al.

(10) Patent No.: US 9,527,912 B2
(45) Date of Patent: Dec. 27, 2016

(54) PREVENTION OF IMMUNOLOGICAL REJECTION OF TRANSPLANTED STEM CELLS BY LEUKOCYTE COSTIMULATORY MOLECULE BLOCKADE

(75) Inventors: Jeremy Pearl, San Francisco, CA (US); Joseph Wu, Stanford, CA (US); Mark Davis, Atherton, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 1020 days.

(21) Appl. No.: 13/068,643

(22) Filed: May 16, 2011

(65) Prior Publication Data

US 2011/0293611 A1    Dec. 1, 2011

Related U.S. Application Data

(60) Provisional application No. 61/395,828, filed on May 17, 2010, provisional application No. 61/463,581, filed on Feb. 18, 2011.

(51) Int. Cl.

| | |
|---|---|
| *A61K 35/12* | (2015.01) |
| *C07K 16/28* | (2006.01) |
| *A61K 35/30* | (2015.01) |
| *A61K 35/545* | (2015.01) |
| *A61K 38/17* | (2006.01) |
| *A61K 38/19* | (2006.01) |
| *A61K 39/00* | (2006.01) |

(52) U.S. Cl.
CPC ........... *C07K 16/2845* (2013.01); *A61K 35/30* (2013.01); *A61K 35/545* (2013.01); *A61K 38/1774* (2013.01); *A61K 38/1793* (2013.01); *A61K 38/191* (2013.01); *C07K 16/2875* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 6,280,957 B1* | 8/2001 | Sayegh et al. | ................ 435/7.1 |
| 7,455,835 B2 | 11/2008 | Cohen et al. | |
| 2002/0039577 A1 | 4/2002 | Townsend et al. | |
| 2003/0072754 A1 | 4/2003 | Kenyon et al. | |
| 2008/0160022 A1 | 7/2008 | Larsen et al. | |
| 2008/0254004 A1 | 10/2008 | Terskikh et al. | |
| 2009/0028850 A1 | 1/2009 | Rother et al. | |
| 2009/0148404 A1 | 6/2009 | Berenson et al. | |

OTHER PUBLICATIONS

Graves et al., Transplantation, 2009, v.15, pp. 1-12.*
Grinnemo; et al., "Costimulation Blockade Induces Tolerance to HESC Transplanted to the Testis and Induces Regulatory T-Cells to HESC Transplanted into the Heart", Stem Cells (2008), 26:1850-1857.
Gudmundsdottir; et al., "T Cell Costimulatory Blockade: New Therapies for Transplant Rejection", J Am Soc Nephol (1999), 10:1356-1365.
Kirk; et al., "CTLA4-Ig and anti-CD40 ligand prevent renal allograft rejection in primates", PNAS (1997), 94:8789-8794.
Little; et al., "The future of allogeneic hematopoietic stem cell transplantation: minimizing pain, maximizing gain", The Journal of Clinical Investigation (2000), 105(12)::1679-1681.
Pree; et al., "New approaches to prevent transplant rejection: Co-stimulation blockers anti-CD4OL an dCTLA4Ig", Drug Discovery Today: Therapeutic Strategies (2006), 3(1):41-47.
Wekerle; et al., "Extrathymic T Cell Deletion and Allogeneic Stem Cell Engraftment Induced with Costimulatory Blockade Is Followed by Central T Cell Tolerance", The Journal of Experimental Medicine (1998), 187(12):2037-2044.

* cited by examiner

*Primary Examiner* — Michail Belyavskyi
(74) *Attorney, Agent, or Firm* — Pamela J. Sherwood; Bozicevic, Field & Francis LLP

(57) ABSTRACT

Compositions and methods are provided for transplantation of pluripotent stem cells and differentiated cells derived therefrom.

7 Claims, 7 Drawing Sheets
(7 of 7 Drawing Sheet(s) Filed in Color)

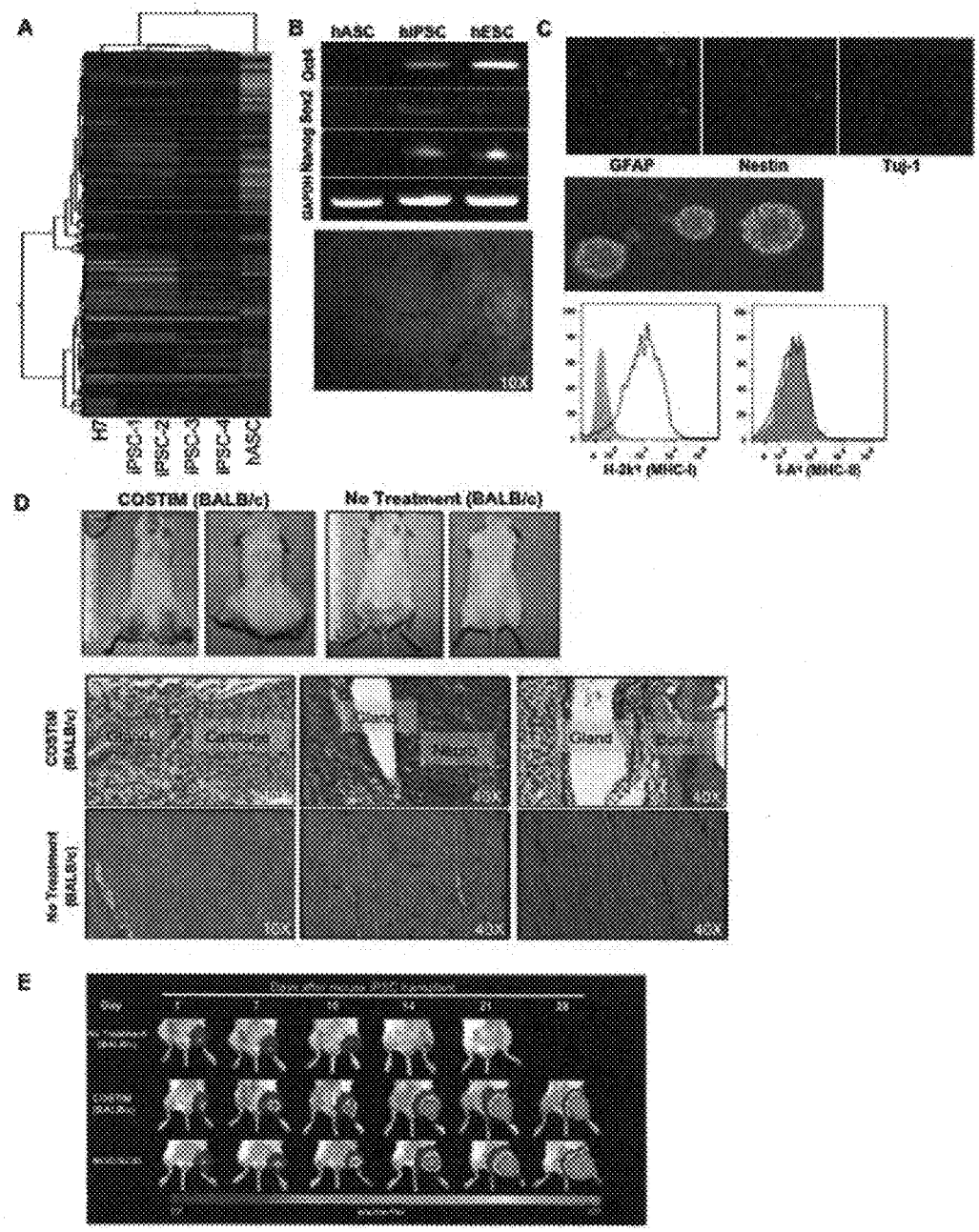

PREVENTION OF IMMUNOLOGICAL REJECTION OF TRANSPLANTED STEM CELLS BY LEUKOCYTE COSTIMULATORY MOLECULE BLOCKADE

BACKGROUND OF THE INVENTION

Regenerative medicine is the process of creating living, functional tissues to repair or replace tissue or organ function lost due to age, disease, damage, or congenital defects. This field holds the promise of regenerating damaged tissues and organs in the body by introducing outside cells, tissue, or even whole organs to integrate and become a part of tissues or replace whole organ. Importantly, regenerative medicine has the potential to solve the problem of the shortage of organs available for donation compared to the number of patients that require life-saving organ transplantation.

One key to the success of regenerative medicine strategies has been the ability to isolate and generate stem cells, including pluripotent stem cells. In one aspect, pluripotent stem cells can be differentiated into a necessary cell type, where the mature cells are used to replace tissue that is damaged by disease or injury. This type of treatment could be used to replace neurons damaged by spinal cord injury, stroke, Alzheimer's disease, Parkinson's disease, or other neurological problems. Cells grown to produce insulin could treat people with diabetes and heart muscle cells could repair damage after a heart attack. This list could conceivably include any tissue that is injured or diseased.

The generation of pluripotent stem cells that are genetically identical to an individual provides unique opportunities for basic research and for potential immunologically-compatible novel cell-based therapies. Methods to reprogram primate somatic cells to a pluripotent state include differentiated somatic cell nuclear transfer, differentiated somatic cell fusion with pluripotent stem cells, and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

A significant first hurdle in stem cell-based therapy is the differentiation of pluripotent cells into a desired tissue type. Such methods currently rely on the step-wise introduction of factors and conditions to guide the cells down a developmental pathway, resulting eventually in a mature or committed progenitor cell that can transplanted into a patient.

Embryonic stem cells (ESCs) are an attractive source for tissue regeneration and repair therapies because they can be cultured indefinitely in vitro and can be differentiated into virtually any cell type in the adult body. However, for this approach to succeed, the transplanted ESCs must engraft successfully and survive long enough to permit a therapeutic benefit. An important obstacle facing the engraftment and function of hESCs is transplant rejection by the immune system. The present invention addresses this issue.

SUMMARY OF THE INVENTION

Composition and methods are provided for increasing the survival of stem cell and stem cell derived cells during the process of transplantation. The immunosuppressive approach of the present invention combines agents that block one or more, usually two or more leukocyte costimulatory molecules, and may block 3 or more leukocyte costimulatory molecules, where the cocktail of leukocyte costimulatory molecule blocking agents provides for long-term engraftment when administered for a short period of time, usually less than about 4 weeks, less than 2 weeks, or even less than 1 week. In some embodiments of the invention the leukocyte costimulatory molecules are selected from CD40L, LFA-1 and CTLA4. The transplantation may be performed in the absence of small molecule immunosuppressants such as cyclosporine A, tacrolimus, mycophenylate mofetil, rapamycin, and the like.

Cells of interest include differentiated and progenitor cells, which may be derived from tissue sources of progenitor cells or may be derived from the differentiation of suitable stem cells, including embryonic stem cells, induced pluripotent stem cells, etc., where the differentiation is optionally performed in vitro or ex vivo. Various differentiated cells derived from pluripotent cells in vitro include cardiomyocytes, neuronal cells, e.g. neurons, neural progenitors, oligodendrocytes, etc.; pancreatic cells and progenitors thereof, e.g. beta cells, alpha cells, etc.; hematopoietic cells, e.g. hematopoietic stem cells and lineage committed progenitor cells; muscle cells; and the like.

In one embodiment, methods are provided for transplantation, the method comprising administering to a recipient during transplantation of cells derived from stem cells in vitro, a cocktail of leukocyte costimulatory molecule blocking agents, for a period of time sufficient to provide for long term engraftment, usually less than about 4 weeks. Optionally, the method further comprises detection of viable cells following transplantation.

In another embodiment, compositions are provided for use in transplantation. Such compositions may comprise a cocktail of leukocyte costimulatory molecule blocking agents, in a form suitable for administering with cells during transplantation into a recipient. Such a composition may further comprise suitable buffers and/or excipients appropriate for transfer into an animal. Such compositions may further comprise cells to be engrafted.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5. Allogeneic and xenogeneic transplantation of iPSCs results in immune rejection which is mitigated by costimulatory molecule blockade. (a) Pearson hierarchical clustering demonstrating that the four hiPSC lines are similar to H7 hESC line and distinct from human adipose stromal cells (hASCs). The hASC and H7 data are each the average of biological duplicates. Red=upregulated transcript, green=downregulated transcript. (b) Upper panel: RT-PCR comparing the expression of pluripotency transcription factors (Oct4, Sox2, and Nanog) among hASCs, hASC-derived iPSCs, and H7 hESCs. Lower panel: phase contrast image demonstrating that hiPSCs can be differentiated into multiple cell types, including endothelial cells and beating cardiomyocytes. (c) Top panel: immunostaining of miPSC-NSC for multiple neural stem cell markers; middle panel: brightfield microscopy demonstrating miPSC-NSC neurosphere morphology; bottom panel: flow cytometric analysis of MHC expression by miPSC-NSCs. (d) Images of immunocompetent mice 21 days after bilateral intramuscular (gastrocnemius) transplantation of undifferentiated unlabeled hiPSCs show enlarged hindlimb size in COSTIM treated as opposed to untreated animals. Corresponding H&E stained muscle sections show presence of hiPSC-derived teratoma in COSTIM treated mice, whereas no signs of teratoma formation are observed in untreated mice. (e) BLI of miPSC survival upon allogeneic (BALB/c) transplantation into mice receiving no treatment or costimulatory blockade (COSTIM) treatment. n=3-4 per group.

DETAILED DESCRIPTION OF THE INVENTION

Figure 1:
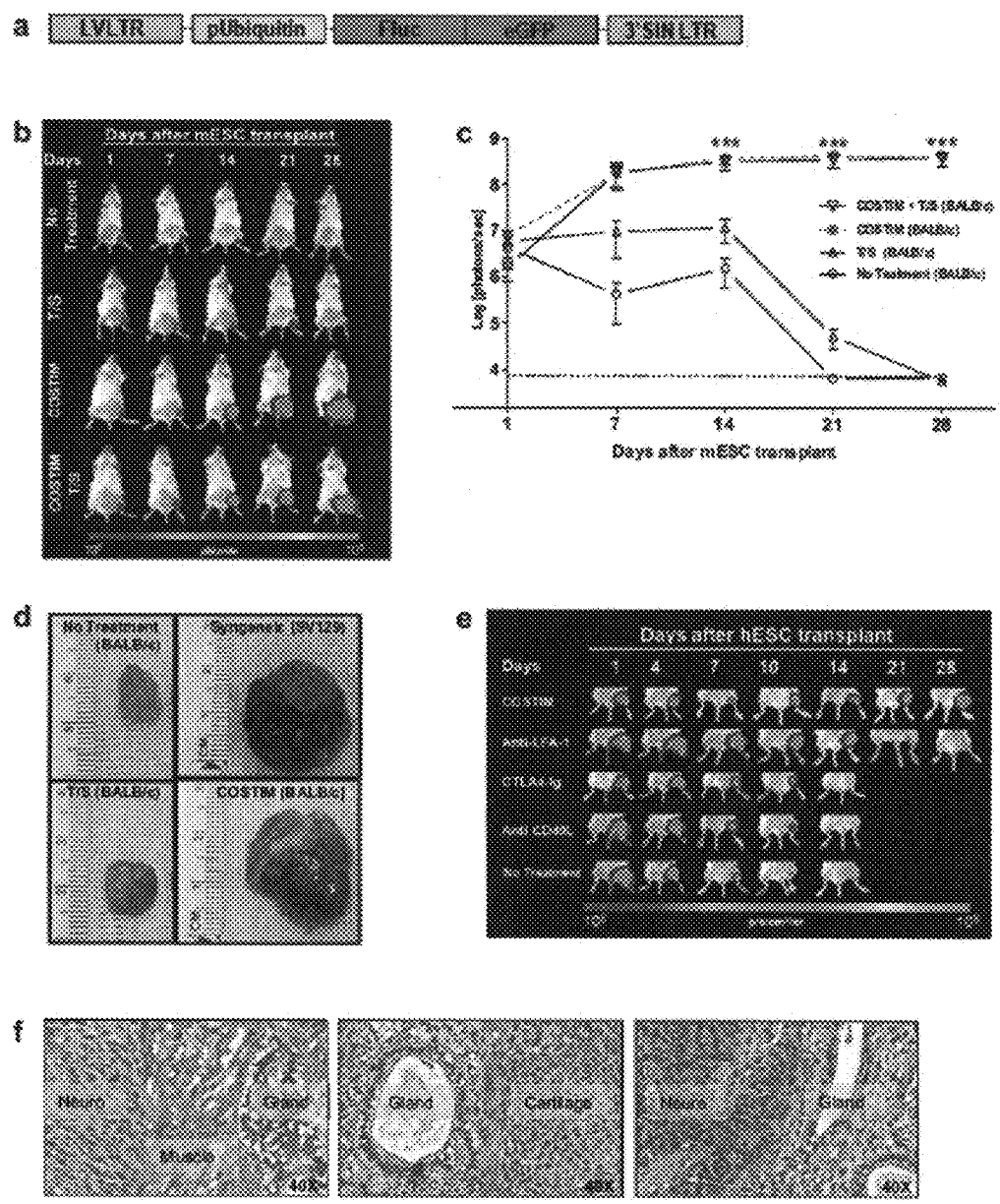
FIG. 1. Blockade of leukocyte costimulatory molecules mitigates allogeneic and xenogeneic transplantation rejection of undifferentiated ESCs. (a) Schema of the DF reporter gene construct containing Fluc and eGFP driven by a constitutive human ubiquitin promoter, using a self-inactivating (SIN) lentiviral vector. (b) Representative bioluminescence images and (c) quantitative bioluminescence intensity of mESC-transplanted mice that received either no treatment, TAC+SIR (T/S), CTLA4-Ig+anti-LFA-1+anti-CD40L (COSTIM), or COSTIM+T/S. n=5 per group, ***P<0.001. (d) Representative images of gastrocnemius muscles 28 days after transplantation of non-transduced mESCs. (e) Representative bioluminescence images of xenogeneic hESC-transplanted mice that received either no treatment, mono-therapy, or a combination of all three costimulatory blockade agents (COSTIM). n=5-8 per group. (f) Histopathological evaluation of HE-stained muscle sections from COSTIM treated mice demonstrating hESC-derived teratoma formation. All values are expressed as mean±s.e.m. Color scale bars are in photons per second per squared-centimeter per steridian (p/s/cm$_2$/sr). HE, haematoxylin and eosin stain.

Compositions and methods are provided for transplantation of stem cells, including pluripotent stem cells, e.g. iPS cells, embryonic stem cells, etc. and for the transplantation of differentiated cells derived from such stem cells, usually derived from such stem cells in vitro.

A cell transplant, as used herein, is the transplantation of one or more cells into a recipient body, usually for the purpose of augmenting function of an organ or tissue in the recipient. As used herein, a recipient is an individual to whom tissue or cells from another individual (donor), commonly of the same species, has been transferred. Generally the MHC antigens, which may be Class I or Class II, will be matched, although one or more of the MHC antigens may be different in the donor as compared to the recipient. The graft recipient and donor are generally mammals, preferably human. Laboratory animals, such as rodents, e.g. mice, rats, etc. are of interest for drug screening, elucidation of developmental pathways, etc. For the purposes of the invention, the cells may be allogeneic, autologous, or xenogeneic with respect to the recipient.

Cells of interest for transfer include, without limitation, cardiomyocytes and progenitors thereof; neural progenitor cells; pancreatic islet cells, particularly pancreatic β-cells; hematopoietic stem and progenitor cells; mesenchymal stem cells; muscle satellite cells; and the like.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "pluripotency" and pluripotent stem cells it is meant that such cells have the ability to differentiate into all types of cells in an adult organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPS cells" it is meant that the differentiated somatic cells can be induced to become, i.e. can be reprogrammed to become, iPS cells. In other words, the somatic cell can be induced to redifferentiate so as to establish cells having the morphological characteristics, growth ability and pluripotency of pluripotent cells. iPS cells have an hESC-like morphology, growing as flat colonies with large nucleo-cytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, pluripotent cells are capable of forming teratomas. In addition, they are capable of forming or contributing to ectoderm, mesoderm, or endoderm tissues in a living organism.

Stem cells and cultures thereof. Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hES-BGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human iPS and human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2): 205-16; etc.) The stem cells may be obtained from any mammalian species, e.g. human, equine, bovine, porcine, canine, feline, rodent, e.g. mice, rats, hamster, primate, etc.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection.

Progenitor or Differentiated Cells.

A "differentiated cell" is a cell that has progressed further down the developmental pathway than the cell it is being compared with. Thus, embryonic stem cells can differentiate to lineage-restricted progenitor cells (such as a mesodermal stem cell), which in turn can differentiate into other types of progenitor cells further down the pathway (such as an cardiomyocyte progenitor), and then to an end-stage differentiated cell, which plays a characteristic role in a certain tissue type, and may or may not retain the capacity to proliferate further. For the purposes of the present invention, progenitor cells are those cells that are committed to a lineage of interest, but have not yet differentiated into a mature cell.

The potential of ES cells to give rise to all differentiated cells provides a means of giving rose to any mammalian cell type, and so a very wide range of culture conditions may be used to induce differentiation, and a wide range of markers may be used for selection. One of skill in the art will be able to select markers appropriate for the desired cell type.

Among the differentiated cells of interest are cells not readily grown from somatic stem cells, or cells that may be required in large numbers and hence are not readily produced in useful quantities by somatic stem cells. Such cells may include, without limitation, neural cells, oligodendrocytes, pancreatic islet cells, hematopoietic cells, cardiac muscle cells, etc.

For example, NCAM may be used as a marker for the selection of aggregates comprising neural lineage cells, inter alia (see Kawasaki et al. (2002) PNAS 99:1580-1585). Neuronal subpopulations can be derived from in vitro differentiation of embryonic stem (ES) cells by treatment of embryo-like aggregates with retinoic acid (RA). The cells express Pax-6, a protein expressed by ventral central nervous system (CNS) progenitors. CNS neuronal subpopulations generated expressed combinations of markers characteristic of somatic motoneurons (Islet-1/2, Lim-3, and HB-9), cranial motoneurons (Islet-1/2 and Phox2b) and interneurons (Lim-1/2 or EN1) (Renoncourt et al. (1998) Mech Dev. 179(1-2):185-97; Harper et al. (2004) PNAS 101(18):7123-8).

Another lineage of interest is pancreatic cells. The pancreas is composed of exocrine and endocrine compartments. The endocrine compartment consists of islets of Langerhans, clusters of four cell types that synthesize peptide hormones: insulin ($\beta$ cells), glucagon ($\alpha$ cells), somatostatin ($\gamma$ cells), and pancreatic polypeptide (PP cells). Although the adult pancreas and central nervous system (CNS) have distinct origins and functions, similar mechanisms control the development of both organs. Strategies that induce production of neural cells from ES cells can be adapted for endocrine pancreatic cells. Useful culture conditions include plating EBs into a serum-free medium, expansion in the presence of basic fibroblast growth factor (bFGF), followed by mitogen withdrawal to promote cessation of cell division and differentiation.

Expression of nestin may be useful as a marker for selection of a number of progenitor cells from embryoid bodies. The cells in the pancreatic lineages express GATA-4 and HNF3, as well as markers of pancreatic $\beta$ cell fate, including the insulin I, insulin II, islet amyloid polypeptide (IAPP), and the glucose transporter-2 (GLUT 2). Glucagon, a marker for the pancreatic a cell, may also induced in differentiated cells. The pancreatic transcription factor PDX-1 is expressed. These ES cell-derived differentiating cells have been shown to self-assemble into structures resembling pancreatic islets both topologically and functionally (Lumelsky et al. (2001) Science 292(5520):1389-94.

Derivation of hematopoietic lineage cells is also of interest. Hematopoietic stem cells and precursors have been well-characterized, and markers for the selection thereof are well known in the art, e.g. CD34, CD90, c-kit, etc. Co-culture of human ES cells with irradiated bone marrow stromal cell lines in the presence of fetal bovine serum (FBS), but without other exogenous cytokines, leads to differentiation of the human ES cells within a matter of days.

A portion of these differentiated cells express CD34, the best-defined marker for early hematopoietic cells (Kaufman and Thomson (2002) J. Anat. 200(Pt 3):243-8). CD34+ and CD34+CD38− cells derived from ES cell cultures have a high degree of similarity in the expression of genes associated with hematopoietic differentiation, homing, and engraftment with fresh or cultured bone marrow (Lu et al. (2002) Stem Cells 20(5):428-37.

A "cardiomyocyte precursor" is defined as a cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

A co-stimulatory molecule as used herein refers to a molecule such as B7, CD40 etc expressed on the surface of a cell and which is capable of interacting with a receptor on the surface of an immune cell. Receptors for co-stimulatory molecules include but are not limited to LFA-1, fas ligand, CD28, CTLA4, and CD40 ligand. The receptors are generally found on the surface of cells such as CD4 T cells, CD8 T cells, NK cells, gamma delta T cells, dendritic cells, B cells and macrophage. In addition to these cells, cells expressing such receptors or functional fragments thereof may be generated using routine procedures known in the art such as transfection.

An optimal T cell response requires two-signals, ligation of the antigen-specific T cell receptor (TCR) (signal 1) and an accessory signal from a non-antigen specific costimulatory molecule (signal 2). When only signal 1 is provided without signal 2, T cell activation is disturbed and the cell may adopt a state of anergy, undergo apoptosis, abortive proliferation, or immunoregulation. Among the costimulatory interactions for T-cell activation are CD80/CD86 on antigen presenting cells (APC) interacting with CD28 on T-cells and CD40 on APCs engaging CD40-ligand on T-cells. Negatively regulating costimulatory molecules have also been described, particularly CTLA4, which is expressed by activated T-cells and binds to CD80/CD86 with 10-20-fold greater affinity than CD28. Upon engagement, CTLA4 delivers an inhibitory signal to the T-cell. Lastly, LFA-1 is involved in the formation of the immunological synapse as well as the trafficking and costimulation of T-cells.

The CTLA-4/CD28/B7 system is a group of proteins involved in regulating T-cell proliferation through this secondary signaling pathway. The T-cell proliferative response is controlled by the interaction of the B7 family of proteins, which are expressed on the surface of APCs, with CTLA-4 and CD28. The B7 family of proteins is composed of structurally related glycoproteins including B7-1, B7-2, and B7-3 (Galea-Lauri et al., Cancer Gene Therapy, v. 3, p. 202-213 (1996); Boussiotis, et al., Proc. Nat. 4cad. Sci. USA, v. 90, p. 11059-11063 (1993)).

CD28, a homodimeric glycoprotein having two disulfide linked 44-kd subunits, is found on 95% of CD4+ and 50% of CD8+ cells. Studies using monoclonal antibodies reactive with CD28 have demonstrated that CD28 is involved in a secondary signal pathway in the activation of T-cell proliferation. Antibodies which block the interaction of CD28 with its ligand have been found to inhibit T-cell proliferation in vitro resulting in antigen specific T cell anergy.

Costimulatory receptor blocking agents are known in the art. Examples of such agents include, but are not limited to anti-CD40 antibodies, anti-CD40L antibodies (e.g., MR1 (MRI) or 5C8), anti-B7 antibodies (for example, anti-B71 antibodies and anti-B72 antibodies), anti-CTLA4 antibodies, B7-Ig, CD28-Ig, CTLA4-Ig, CD40-Ig and CD40L-Ig. Costimulation blockade agents also include the extracellular domain of any of the surface proteins in soluble form, including soluble extracellular CD40, CD40L, B7, CD28 or CTLA4 domain proteins or derivatives thereof, or any substance which is a receptor antagonist, or which blocks costimulation at an intracellular or extracellular level. Soluble CD40 ligands can, for example, be made by the methods disclosed in U.S. Pat. No. 5,540,926, issued Jul. 30, 1996 to Alejandro et al., and in EP 555880 issued to Aruffo et al., Aug. 18, 1993, the entire contents of which are incorporated herein by reference. Fusion proteins, including B7-Ig, CD28-Ig, CTLA4-Ig, CD40-Ig and CD40L-Ig can be made using the methods disclosed in Strom et al., WO 9631229, published Oct. 10, 1996; Linsley et al., U.S. Pat. No. 5,580,756 issued Dec. 3, 1996; Linsley et al., U.S. Pat. No. 5,521,288, issued May 28, 1996; Linsley et al., U.S. Pat. No. 5,434,131, issued Jul. 18, 1995; the entire contents of all which are incorporated herein by reference. Methods of making and using antibodies and ligands, for example anti-B7.1 antibodies and other B7.1 ligands are disclosed, for example in deBoer et al., U.S. Pat. No. 5,747,034 issued May 5, 1998 and, for example, anti-CD40 ligand antibody and soluble CD40 are disclosed in Noelle et al., U.S. Pat. No. 5,683,693, issued Nov. 4, 1997, the entire contents of both of which are herein incorporated by reference in their entirety.

In a preferred embodiment, the blockade comprises at least two agents, for example, anti-CD40L and CTLA4-Ig, and may include at least 3 agents, e.g. anti-CD40L, CTLA4-Ig and anti-LFA-1.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Methods of Transplantation

Ex vivo and in vitro differentiated cell populations useful as a source of cells may be obtained from any mammalian species, e.g. human, primate, equine, bovine, porcine, canine, feline, etc., particularly human cells. Ex vivo and in vitro differentiated cell populations may include fresh or frozen cells, which may be from a neonate, a juvenile or an adult, and differentiated tissues including skin, muscle, blood, liver, pancreas, lung, intestine, stomach, and other differentiated tissues. Pluripotent cells are optionally deleted from the differentiated cell population prior to introduction into the recipient. The dose of cells will be determined based on the specific nature of the cell, recipient and nature of condition to be treated, and will generally include from about $10^6$-$10^{10}$ cells, which may be provided in suspension, as aggregates, and the like.

To determine the suitability of cell compositions for therapeutic administration, the cells can first be tested in a suitable animal model. At one level, cells are assessed for their ability to survive and maintain their phenotype in vivo. Cell compositions may be administered to immunodeficient animals (such as nude mice, or animals rendered immunodeficient chemically or by irradiation). Tissues are harvested after a period of regrowth, and assessed as to whether the administered cells or progeny thereof are still present. This can be performed by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to, published sequence data.

The differentiated, progenitor or stem cells may be used for tissue reconstitution or regeneration in a human patient or other subject in need of such treatment. The cells are administered in a manner that permits them to graft or migrate to the intended tissue site and reconstitute or regenerate the functionally deficient area.

The differentiated, progenitor or stem cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types, especially endothelial cells.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over a 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type.

A cocktail of leukocyte costimulatory blocking molecules is administered to the transplantation recipient for a period of time sufficient to provide for long term engraftment, i.e. where long term engraftment refers to detectable levels of donor cells after at least about 1 month, usually after at least about 2 months, after at least about 3 months, after at least about 6 months, after at least about 1 year, or more.

The cocktail of leukocyte costimulatory molecule blocking agents includes at least one agent, usually at least 2 agents, and may include 3 agents or more. Various combinations of molecules are contemplated, of which CTLA4-Ig, anti-LFA-1, and anti-CD40L are one possible combination.

The initial dose of cocktail may be administered at or around the time the donor cells are introduced to the recipient, i.e. within about 12 hours of introduction. The cocktail of agents, or a subset of the agents, may then be administered at time points following the donor cell introduction, for example at daily, semi-daily, or every 2 days, etc. The leukocyte costimulatory molecule blocking agents are generally administered for a short period of time, usually less than 4 week from start of transplantation, less than 3 weeks, less then 2 weeks, and may be less than 10 days, less than 8 days, less than or about 6 days.

The therapeutic dose of each component of the leukocyte costimulatory molecule blocking cocktail may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary, e.g. to provide for long term engraftment.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The formulation herein may also contain more than one active compound as necessary for the particular indication being treated, preferably those with complementary activities that do not adversely affect each other.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody or cocktail of antibodies. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

For further elaboration of general techniques useful in the practice of this invention, the practitioner can refer to standard textbooks and reviews in cell biology, tissue culture, and embryology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Example 1

Leukocyte Costimulatory Molecule Blockade Permits Allogeneic and Xenogeneic Engraftment of Pluripotent Stem Cells Here we show that blocking the action of leukocyte costimulatory molecules permits long-term ESC engraftment. Using non-invasive in vivo imaging, we show the spatiotemporal kinetics of pluripotent cell rejection and the success of this immunosuppressive therapy for mouse ESC (mESC), human ESC (hESC), mouse induced pluripotent stem cell (miPSC), human iPSC (hiPSC), and more differentiated ESC-derivatives. Additionally, we provide in vitro, in vivo, and gene expression based-evidence describing the mechanism by which inhibition of costimulatory molecules suppresses T-cell activation. This report shows that a short-term immunosuppressive approach is capable of inducing long-term engraftment and tolerance to transplanted ESCs and iPSCs, and marks a significant step forward in improving our mechanistic understanding of the critical role costimulatory molecules play in leukocyte activation.

Traditional immunosuppressive therapies (e.g., Tacrolimus, Sirolimus, and mycophenolate mofetil) provide only marginal improvements in ESC survival, with little evidence of cell engraftment past 3-4 weeks post transplantation. Furthermore, traditional immunosuppression requires chronic administration, rendering the host immune system compromised and vulnerable to opportunistic infections. Thus the ideal therapy should involve only a brief period of immunosuppression, but induce a specific long-lasting tolerance to the donor cells. With this goal in mind, we tested whether or not a brief course of treatment with three costimulatory receptor blocking agents: CTLA4-Ig (Abatacept), anti-CD40-ligand (anti-CD40L), and anti-LFA-1, could induce long-term allogeneic and xenogeneic ESC engraftment.

An optimal T cell response requires two-signals, ligation of the antigen-specific T cell receptor (TCR) (signal 1) and an accessory signal from a non-antigen specific costimulatory molecule (signal 2). When only signal 1 is provided without signal 2, T cell activation is disturbed and the cell may adopt a state of anergy, undergo apoptosis, abortive proliferation, or immunoregulation. Among the most important costimulatory interactions for T-cell activation are CD80/CD86 on antigen presenting cells (APC) interacting with CD28 on T-cells and CD40 on APCs engaging CD40-ligand on T-cells. Negatively regulating costimulatory molecules have also been described, particularly CTLA4, which is expressed by activated T-cells and binds to CD80/CD86 with 10-20-fold greater affinity than CD28. Upon engagement, CTLA4 delivers an inhibitory signal to the T-cell. Lastly, LFA-1 is involved in the formation of the immunological synapse as well as the trafficking and costimulation of T-cells.

The technology used to evaluate transplanted cell survival is of paramount importance for the accurate assessment of immunologic rejection. Until recently, the majority of studies evaluated ESC survival by reporter genes dependent on immunohistochemical staining for β-galactosidase (LacZ) or detection of GFP. But these methods only provide a "snapshot" of cell survival. In contrast, in vivo bioluminescent imaging (BLI) provides longitudinal evaluation of the spatiotemporal kinetics of ESC rejection. In this study, ESCs were transduced with a double fusion (DF) reporter gene construct carrying firefly luciferase (Fluc) and enhanced green florescent protein (eGFP) (FIG. 1a). ESCs robustly expressed Fluc, which correlated with ESC number ($r^2=0.99$) and displayed a tight cluster morphology with robust GFP expression.

We next investigated longitudinal ESC survival after intramuscular (gastrocnemius muscle) transplantation of mESCs into syngeneic (SV129, H-2k$^b$) and allogeneic (BALB/c, H-2k$^d$) mice by in vivo BLI. mESC survival was significantly limited in allogeneic compared to syngeneic mice (P<0.001), with BLI signal decreasing to background levels in allogeneic animals by 21 days post-transplantation. In contrast, syngeneic hosts accepted mESC grafts indefinitely, resulting in teratoma formation (FIG. 1b,c). Having previously demonstrated that the immune response to hESCs is primarily CD4+ T-cell mediated, we therefore investigated the efficacy of immunosuppressive agents which largely target T-cells. Two immunosuppressive agents were chosen based on different mechanisms of action; specifically, calcineurin inhibitors (tacrolimus; TAC) and target of rapamycin inhibitors (sirolimus; SIR). Additionally, the three costimulatory receptor blocking antibodies (CTLA4-Ig, anti-LFA-1, anti-CD40L) were evaluated in an attempt to induce immune tolerance. Importantly, costimulatory blockade was only administered for short-term on days 0, 2, 4, and 6 post-transplantation.

Whereas daily administration of TAC/SIR prolonged mESCs survival only out to 28 days post-transplantation, a surprisingly brief course of costimulatory blockade was sufficient to prevent mESC rejection completely (P<0.001 costimulatory blockade treatment vs. TAC/SIR or no treatment) (FIG. 1b,c). To exclude the possibility that the immune reaction was exclusively targeted towards antigens produced by the DF reporter genes, we transplanted non-transduced mESCs. Similar to mESCs expressing Fluc-eGFP, this treatment permitted long-term engraftment of non-transduced mESCs. Survival of non-transduced mESC was limited in both untreated and TAC/SIR-treated allogeneic hosts with no evidence of transplanted mESC survival at 28 days post-transplantation (FIG. 1d).

We next investigated if costimulatory blockade could prevent immune rejection of hESCs in the more hostile xenogeneic transplantation environment. Without immunosuppression, hESC survival was significantly limited as BLI signal reached background intensity by day 10-14, whereas BLI signal continually increased in the costimulatory blockade treatment group, resulting in long-term engraftment (P<0.01, FIG. 1e). Consistent with BLI data, histological evaluation of the graft site revealed no evidence of hESC survival in untreated animals, but long term engraftment and teratoma formation in costimulatory blockade treated animals (FIG. 10.

Since the combination of three costimulatory blockade agents is capable of inducing hESC engraftment, we next tested whether monotherapy is sufficient. By day 28, BLI signal decreased to background intensity in all monotherapy groups, with the greatest prolongation of hESC survival observed in the anti-LFA-1 group (FIG. 1e).

Figure 2:
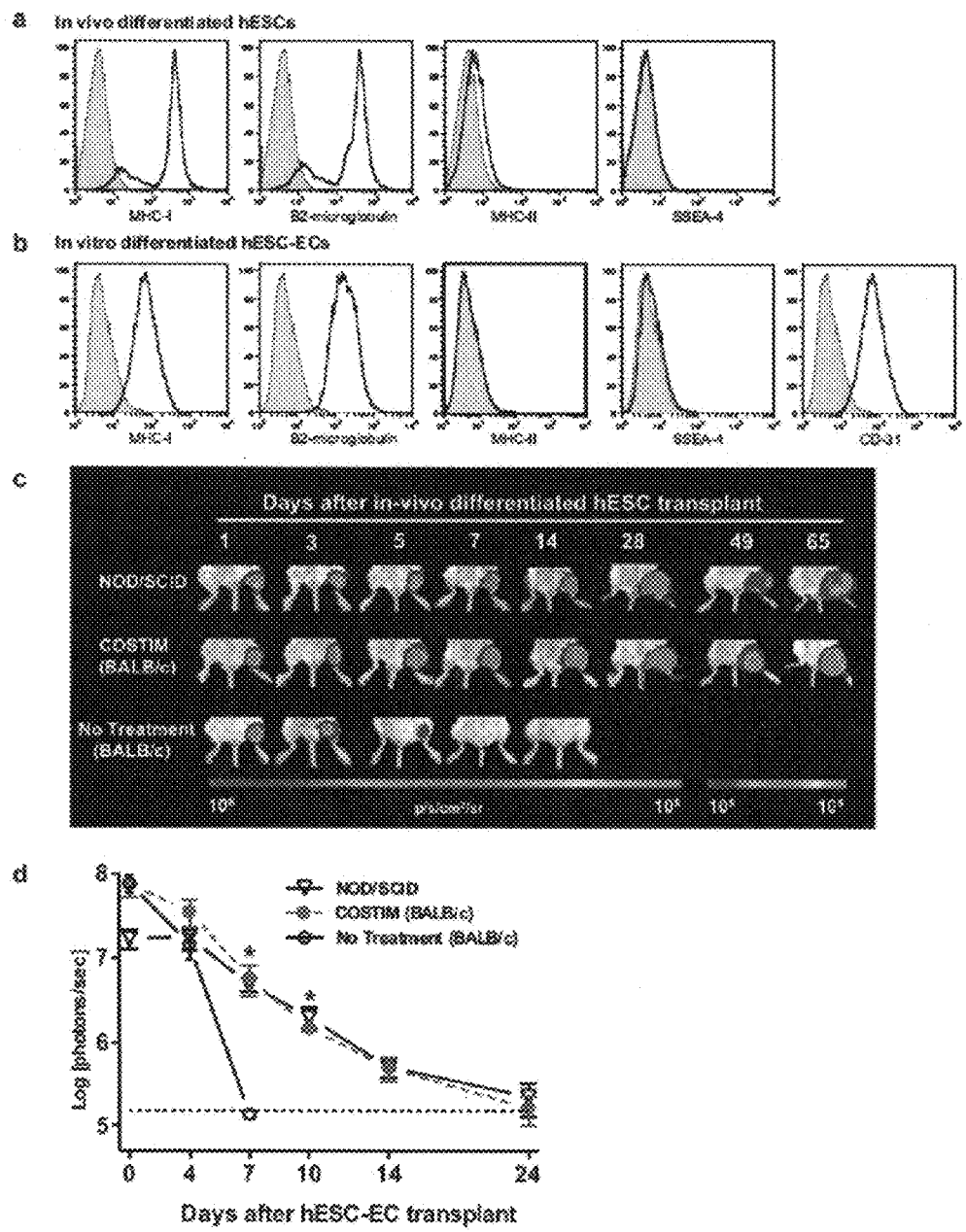
FIG. 2. Leukocyte costimulatory molecule blockade permits long-term engraftment of differentiated hESC-derivatives and hiPSCs. Mean fluorescence intensity of MHC antigens, pluripotency (SSEA-4), and endothelial (CD31) markers on (a) in vivo differentiated hESCs and (b) In vitro differentiated hESC-ECs. Filled histograms represent isotype control antibodies. (c) BLI of the survival of in vivo differentiated hESCs transplanted into immunodeficient (NOD/SCID) and immunocompetent (BALB/) mice that received either costimulatory blockade (COSTIM) or no immunosuppressive treatment, n=3-4 per group. (d) Bioluminescence photon intensities representing the survival of hESC-EC after transplantation into immunodeficient, costimulatory blockade (COSTIM) treated, or non-treated immunocompetent (BALB/c) mice, n=4 per group, *P<0.05. (e) Characterization of hiPSCs by immunostaining with pluripotency markers such as Nanog, Oct4, SSEA-3, SSEA-4, and alkaline phosphatase (AP). (f) hiPSCs and (g) miPSCs in immunodeficient (NOD/SCID) and immunocompetent costimulatory blockade (COSTIM)-treated mice relative to immunocompetent (BALB/c) mice that received no treatment. n=3-5 per group.
Figure 2:
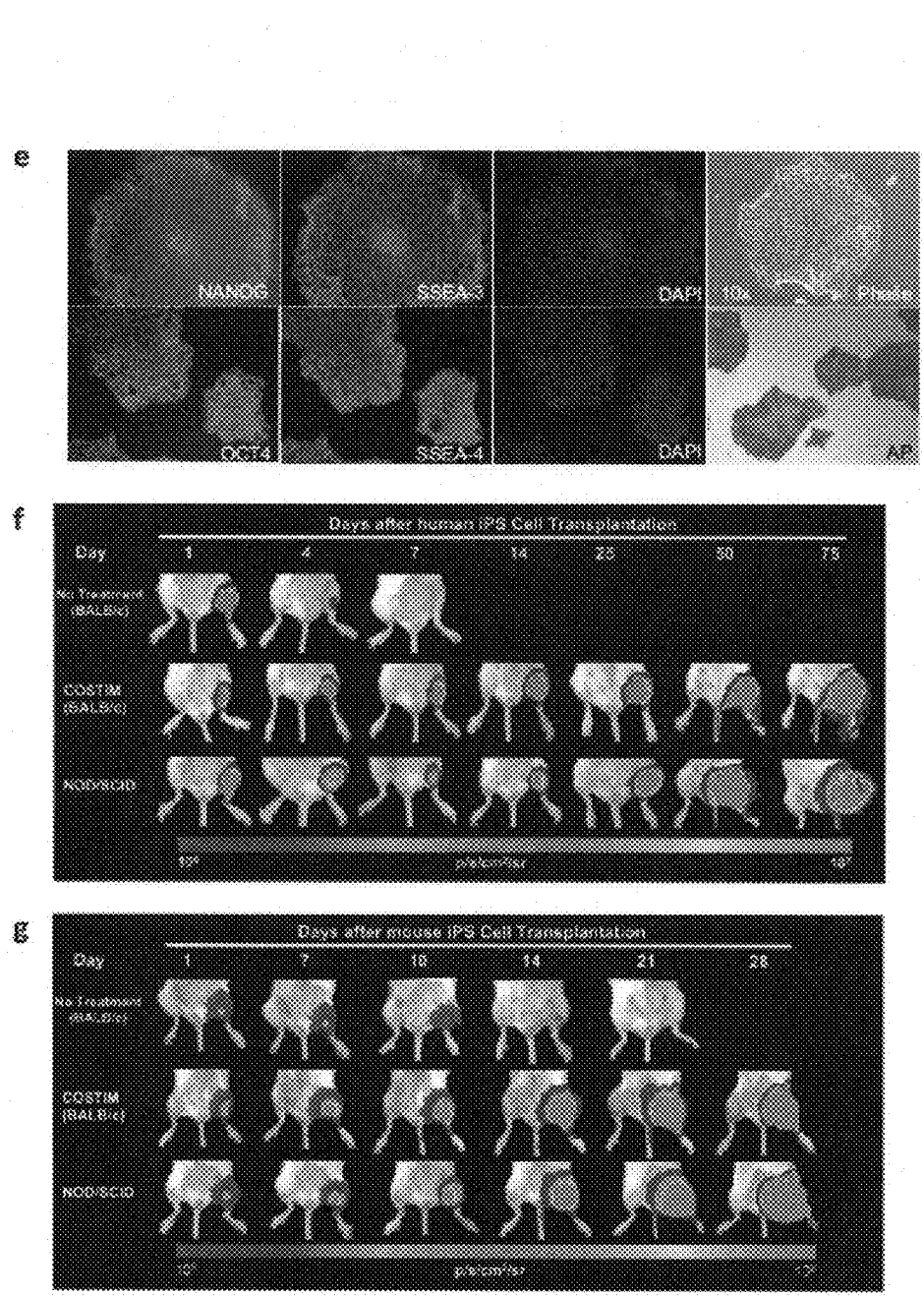

Undifferentiated ESCs have low levels of MHC expression, which increases upon in vivo differentiation (FIG. 2a). These differentiated ESC-derivatives may have impaired survival capacity compared to undifferentiated ESCs when transplanted across histocompatibility barriers. This represents a problem, as it is unlikely that ESC-based therapy will utilize an undifferentiated cell population, but rather, cells will be differentiated into a lineage appropriate for their intended therapy and thus will likely encounter a heightened immune response. We tested the ability of costimulatory blockade to permit engraftment of (1) an in vivo spontaneously differentiated cell population and (2) hESC-derived endothelial cells (hESC-EC). Both cell populations demonstrated increased MHC-I expression relative to undifferentiated cells (FIG. 2a,b). Immunosuppressive treatment with costimulatory blockade permitted long-term engraftment of in vivo differentiated cells (P<0.01 untreated vs. costimulatory blockade treated, FIG. 2c) and engraftment of hESCECs comparable to that observed in immunodeficient NOD/SCID mice (P<0.05 untreated vs. costimulatory blockade treated). Although hESC-ECs did not survive past 24 days (FIG. 2d), we do not attribute this cell death to immune mediated mechanisms because hESC-EC survival in costimulatory blockade treated animals mirrored survival in immunodeficient mice. Instead we attribute the cell death to a phenomena described in the literature as "transplant shock," which is poorly understood but frequently observed, and is thought to arise from a combination of trophic factor deprivation, anoikis, cellular apoptosis, and environmental ischemia.

To circumvent cellular rejection following transplantation, the use of human induced pluripotent stem cells (hiPSC) has been suggested because they can be derived from the recipient and thus may not provoke an immune response. hiPSCs are generated by delivering transcription factors to reprogram somatic cells towards a state of pluripotency$_{16}$. However, it may not be economically feasible to offer this type of treatment to the population at large, nor logistically feasible to safely develop transgenic cells for transplantation on an individual scale. It is possible that the future of this treatment may involve transplantation of an allogeneic cell population and would therefore necessitate immunosuppression.

To assess the immunogenic properties of hiPSCs and the efficacy of costimulatory blockade to induce long-term engraftment of hiPSCs, we created four hiPSC lines from human adipose stem cells (hASC) isolated from four different patients. These hiPSC colonies stained positive for the pluripotency markers, alkaline phosphatase (AP), Nanog, SSEA-3, SSEA-4, and Oct4 (FIG. 2e). Compared to undifferentiated hESCs, the hiPSCs demonstrated similar surface expression levels of pluripotency marker SSEA-4, lack of MHC-II, and slightly higher levels of MHC-I. We preformed microarray gene expression analyses which demonstrated that the four iPSC lines are similar to H7 hESCs (Wicell) and distinct from hASCs (Supplemental FIG. S4a,b). The pluripotency of hiPSCs was examined through the formation of embryoid bodies (EBs). hiPSCEBs expressed multiple markers corresponding to each of the three embryonic germ layers. The hiPSC-EBs demonstrated the capacity for multi-lineage differentiation as we were able to derive neurons, endothelial cells, and beating cardiomyocytes. Upon transplantation into immunocompetent mice, hiPSC survival was significantly limited in untreated compared with costimulatory blockade treated mice (P<0.01, FIG. 2f). BLI signal decreased to background levels in untreated animals by 7 days post-transplantation, whereas long-term engraftment and teratoma formation were observed in costimulatory blockade treated animals.

We next generated mouse iPSCs (miPSC) from FVB (H-2k$^q$) mice and investigated miPSC survival after transplantation into allogeneic (BALB/c, H-2k$^d$) mice by in vivo BLI. In the absence of immunosuppression, transplanted miPSC survival was significantly limited to 14 to 21 days post transplantation. However, when allogeneic mice were treated with costimulatory blockade, long-term engraftment (FIG. 2h) and teratoma formation were observed.

To address the mechanism by which costimulatory blockade permits engraftment of pluripotent cells and their differentiated derivatives, we next examined the effect of costimulatory blockade on both the ESCs and the host. One possible mechanism by which the agents support engraftment is to stimulate increased ESC proliferation. To test this, we transplanted undifferentiated hESCs into immunodeficient mice randomized to receive either costimulatory blockade or saline as control. Between the two groups, we observed no significant difference in the kinetics of hESC proliferation and teratoma formation (FIG. 3a), suggesting these agents do not improve survival by stimulating increased cell proliferation.

We next investigated the effect of costimulatory blockade on ESC viability by comparing the percentage of ESCs undergoing early or late apoptosis. There was no significant difference between ESCs exposed to costimulatory blockade and unexposed controls. To evaluate the toxicity of the costimulatory blockade agents on the host, we compared hematologic, renal, hepatic, and metabolic parameters between costimulatory blockade and untreated mice. For all parameters assayed, costimulatory blockade mice demonstrated similar laboratory values as untreated mice. The low toxicity of costimulatory blockade immunosuppression highlights another advantage of costimulatory blockade over traditional immunosuppressive approaches (e.g., TAC and SIR).

Figure 3:
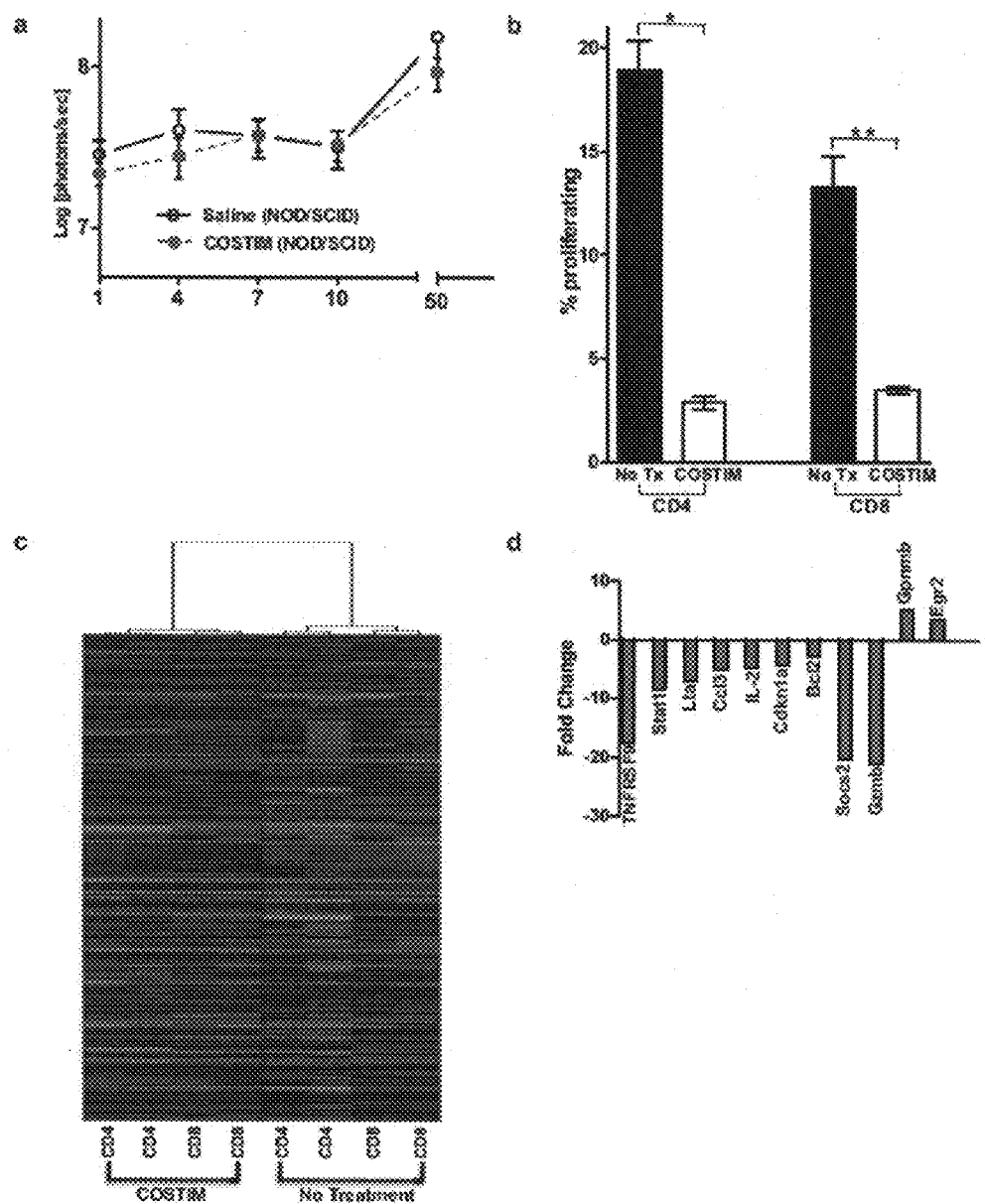
FIG. 3. Gene expression and functional characterization of leukocytes treated with costimulatory molecule blockade. (a) Bioluminescence photon intensities representing the survival of hESCs in immunodeficient (NOD/SCID) mice treated with COSTIM or saline as control. n=5 per group. (b) Mixed lymphocyte reaction comparing the proliferation of COSTIM-treated and untreated T-cell subsets stimulated by allogeneic splenocytes. *P<0.0001, **P=0.0002. (c) Hierarchical clustering of T-cells stimulated by allogeneic splenocytes reveals distinct gene expression clusters between COSTIM-treated and untreated T cells. Biological duplicates for each group are shown. (d) Gene expression fold change of COSTIM-treated relative to untreated T-cells. (e) Schematic representation of the functions of differentially expressed genes which might have contributed to the immunosuppressive effect of costimulatory blockade treatment.
Figure 3:
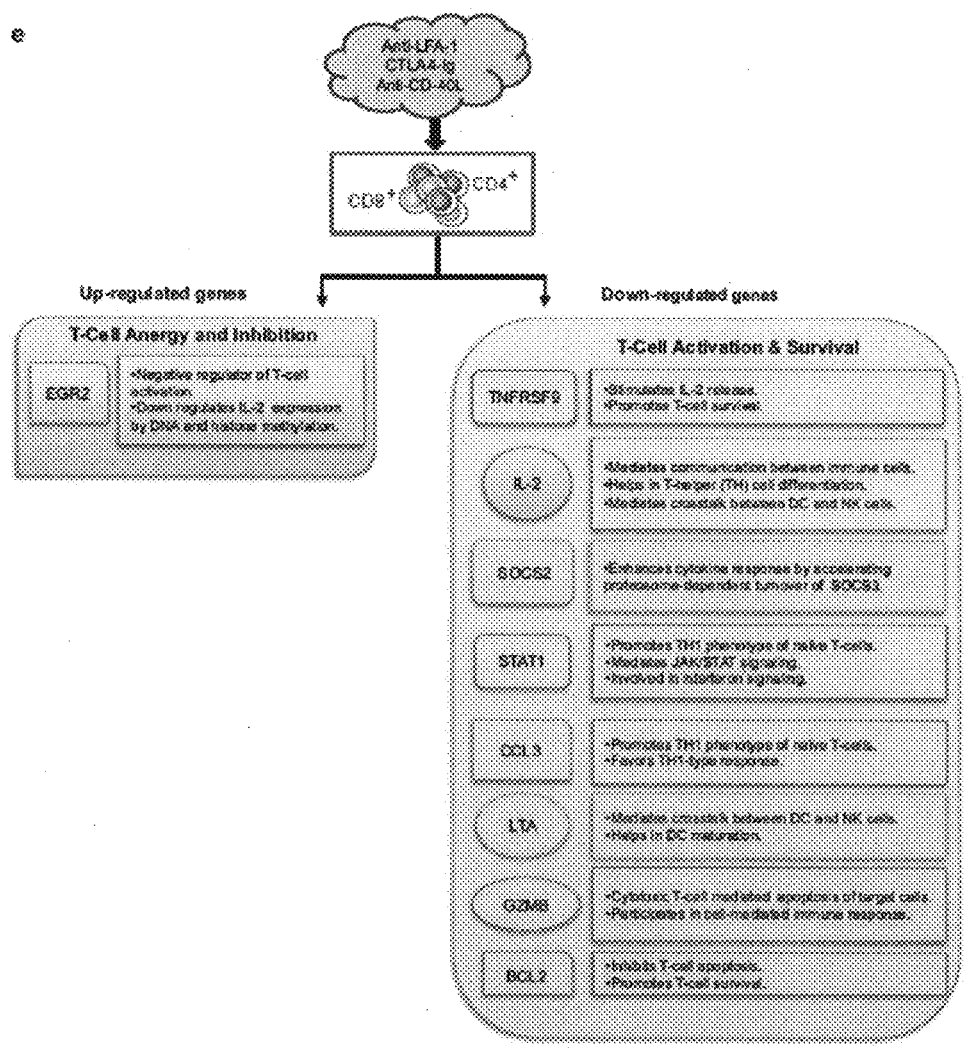

To characterize the effect of costimulatory blockade on the host immune response, we performed mixed lymphocyte reactions (MLR) with MHC mismatched splenocytes as stimulators and responders. Relative to untreated controls, costimulatory blockade significantly mitigated both CD4+ (P<0.0001) and CD8+ (P=0.0002) T-cell proliferation (FIG. 3b).

Certain genetic regulatory programs have previously been described for anergic or for optimally activated T-cells. To elucidate the gene expression "footprint" of costimulatory blockade treated T-cells, we performed microarray gene expression analysis comparing the expression profile of costimulatory blockade treated and untreated responder T-cells. Relative to untreated, the costimulatory blockade treated group had 96 and 40 genes significantly (P<0.05) down- and upregulated, respectively (FIG. 3c,d). From this list we identified key genes previously implicated in the establishment of allograft tolerance and host anergy (FIG. 3e). Many of the genes modulate T-cell expression of IL-2, which was downregulated 4.9-fold in the costimulatory blockade treated splenocytes. 4-1 BB expression was decreased 17.5-fold. 4-1 BB has been implicated in T-cell expansion, pro-inflammatory cytokine induction, upregulation of anti-apoptotic genes, and prevention of activation-induced cell death. SOCS2 accelerates the proteasomal degradation of SOCS3, which is a potent inhibitor of IL2 production. SOCS2 expression was decreased 20.4-fold which is expected to secondarily inhibit IL2 production by decreasing SOCS3 degradation. We also observed a 21.1-fold decrease in the expression of Granzyme B (GZMB), which is a serine protease that is a critical mediator of target-cell apoptosis by CD8 T cells. Expression of BCL-2, an anti-apoptotic protein, was similarly decreased 2.8-fold in costimulatory blockade treated splenocytes$_{26}$. Importantly, Egr-2, a key negative regulator of T cell activation and a critical factor for inducing anergy and immune tolerance, was significantly upregulated in costimulatory blockade-treated splenocytes.

This study demonstrates that a short immunosuppressive course of costimulatory blockade treatment is sufficient to induce long-term engraftment of allogeneic mESCs, miPSCs as well as xenogeneic hESCs, hiPSCs, and their differentiated derivates. Our data suggest that costimulatory blockade permits transplanted cell engraftment by decreasing the expression of pro-inflammatory cytokines (e.g., IL-2, Tnfrsf9), decreasing the polarization of naïve T cells towards a type I phenotype, and increasing the establishment of a pro-apoptotic phenotype and the induction of clonal anergy. Managing transplant rejection in a less harmful way represents a major medical challenge today as well as being a major obstacle to the use of cell-based regenerative therapies in the future. This study demonstrates a short-term immunosuppressive approach which successfully addresses this problem.

Methods Summary

Transduction, transplantation, and in vivo tracking of pluripotent cells: mESC, hESCs and hiPSCs were transduced with a Fluc-eGFP double fusion construct by lentivirus based techniques as previously described[28]. For cell transplantation experiments, $1\times10^6$ human derived and $5\times10^6$ mouse derived cells were injected into the gastrocnemius muscle of recipient mice. Transplanted cell survival was longitudinally monitored via BLI using the Xenogen In Vivo Imaging System (Caliper Life Sciences). Briefly, D-luciferin (Promega) was administered intraperitoneally at a dose of 375 mg/kg of body weight. Animals were placed in a light-tight chamber, and photons emitted from luciferase expressing cells were collected with integration times of 5 sec to 2 min, depending on the intensity of the bioluminescence emission. BLI signal was quantified in maximum photons per second per centimeter square per steradian ($p/s/cm^2/sr$) and presented as $\log_{10}$[photons per second]. For immunosuppressive therapy protocol, female BALB/c mice (8-10 weeks old) were randomized to receive Tacrolimus (TAC; Sigma-Aldrich), Sirolimus (SIR; Rapamune oral solution; Sigma-Aldrich), anti-CD40L (MR-1), anti-LFA-1 (M17/4), or CTLA4-Ig (BioXCell). TAC and SIR were administered once daily by oral gavage, 4 mg/kg/d for TAC and 3 mg/kg/d for SIR. Anti-CD40L, anti-LFA-1, and CTLA4-Ig were administered at a dose of 20 mg/kg on days 0, 2, 4, 6 after transplantation.

Lentiviral production and generation of stable hESC, mESC, and iPSC lines. Self-inactivating (SIN) lentivirus was constructed and the double fusion (DF) Fluc-eGFP construct prepared as previously described. H7 hESCs (Wicell), mouse ES-D3 cells (American Type Culture Collection; ATCC), and hiPSCs derived from human adipose stromal cells (hASC) were transduced with SIN lentivirus with human ubiquitin promoter driving Fluc-eGFP at a multiplicity of infection (MOI) of 10. The eGFP-positive cell populations were analyzed and isolated by florescence activated cell sorting (FACS) on a Vantage SE cell sorter (Becton Dickinson Immunocytometry Systems) followed by plating on feeder layer cells for long-term culturing.

Culture and Transplantation of mESCs.

A murine ES-D3 cell line was generated and maintained on feeder-free 0.2% gelatin-coated six-well plates in DMEM, 10% fetal bovine serum (FBS), 0.1 mmol/L β-mercaptoethanol, 2 mmol/L glutamine, 0.1 mmol/L nonessential amino acids, 100 IU/mL penicillin, 100 μg/mL streptomycin, and $10^3$ units/ml of LIF (Chemicon) to suppress ESC differentiation. The culture medium was changed on a daily basis, and cultures were passaged every two-to-three days. For transplantation, mESCs were trypsinized, washed, and resuspended in a 1:1 mixture of sterile PBS:Matrigel (hESC qualified, BD Biosciences) at $5.0\times10^5$ cells per 30 μl. mESC viability was >95% as determined by flow cytometry using 7-amino-actinomycin D (7-AAD) cell viability solution (eBioscience). mESC transplantation was performed by direct injection into the gastrocnemius muscle of recipient mice using a 28-gauge insulin syringe.

Culture and transplantation of hESCs. hESCs and DF-hESCs (H7 line, Wicell) were initially maintained on top of γ-ray-irradiated mouse embryonic fibroblast (MEF) feeder cells layers. The medium consisted of Dulbecco's modified Eagle's medium (DMEM)/F-12 (Invitrogen), 20% knockout serum replacement (Invitrogen), 0.1 mM nonessential amino acids (Invitrogen), 2 mM L-glutamine (Invitrogen), 0.1 mM β-mercaptoethanol (Sigma), and 8 ng/ml basic fibroblast growth factor (bFGF, Invitrogen). The medium was changed every day and cells were passaged every 3-4 days. Prior to transplantation, hESC colonies were separated from MEF by incubation with dispase (Invitrogen) and subcultured on feeder-free Matrigel (hESC qualified, BD Biosciences) coated six-well plates in mTeSR medium (StemCell Technologies) for three-to-four passages. For transplantation, $1.0\times10^6$ hESCs were prepared as described above for mESC transplantation.

Formation, Isolation, and Transplantation of In Vivo Differentiated hESCs.

In vivo differentiation was induced by intramuscular transplantation of undifferentiated DF-hESCs into costimulatory blockade treated BALB/c mice. Six-weeks later, large visible masses were observed overlying and within the gastrocnemius muscle. Masses were surgically explanted, minced, and digested for 2 h in Collagenase D (2 mg/ml; Worthington Biochemical) at room temperature in RPMI 1640 media (Sigma Chemical Co). To isolate eGFP+ (hESC-derived) cells, digested cell suspensions were run through a 70-μm cell strainer, washed in FACS buffer (PBS 2% FCS), incubated with 7-AAD cell viability solution (eBioscience); isolated by FACS for eGFP+ expression, resuspended, and injected as described above for hESCs.

Differentiation and transplantation of hESC-ECs. Undifferentiated H7 hESC were differentiated into hESC-ECs as previously described. In brief, undifferentiated hESCs were maintained on Matrigel-coated plates as outlined above. To initiate differentiation of hESCs into suspended human embryoid bodies (EBs), the undifferentiated hESCs were transferred to ultra-low attachment plates (Corning) and cultured in differentiation medium containing Iscove's modified Dulbecco's medium (IMDM) and 15% Knockout™ Serum Replacement (Knockout™ SR) (Invitrogen), 1×BIT (BSA, insulin, transferring; StemCell Technologies), 0.1 mM nonessential amino acids, 2 mM L-glutamine, 450 μM monothioglycerol (Sigma), 50 μU/ml penicillin, and 50 μg/ml streptomycin, supplemented with 20 ng/ml bFGF and 50 ng/ml VEGF (R&D Systems). EBs were harvested after 12 days and suspended in rat tail collagen type I (BD Biosciences) at a concentration of 1.5 mg/ml and incubated at 37° C. for 30 min. After the gel polymerized, media was added which consisted of EGM-2 medium (Lonza) containing 5% Knockout™ SR, 50 ng/ml VEGF, and 20 ng/ml bFGF. The cultures were then incubated for 3 days without media change. hESC-ECs were expanded and transplanted as described above for undifferentiated hESCs. FACS analysis of hESCs prior to transplantation demonstrated >85% of cells were CD31+.

Animal Experiments.

8-10 week-old female BALB/c (wild-type), NOD CB17-Prkdcscid/J (NOD/SCID) (Jackson Laboratory), and Sv129 mice (Charles River. Laboratories) were housed at no more than five per cage in our American Association for Accreditation of Laboratory Animal Care-approved facility with 12:12-h light-dark cycles and free access to standard rodent chow and water. All procedures performed were approved by the Animal Care and Use Committee of Stanford University.

FACS Analysis of mESC, hESC, In Vivo Differentiated hESC, hESC-EC, and hiPSC Surface Marker Expression.

Cells were tryspinated, washed, and resupended with FACS buffer (PBS 2% FBS). Mouse cells were incubated with PE-conjugated mouse anti-mouse H-2k$^b$ (AF6-88.5), I-A[b] (AF6-120.1), SSEA-1 (MC480), and SSEA-4 (MC813-70). Human cells were incubated with PE-conjugated mouse anti-human HLA-ABC (G46-2.6), β2-microglobulin (TU99), HLA-DR, DP, DQ (TU39), CD31 (WM59), SSEA-4 (MC813-70), SSEA-1 (MC480) or their respective isotype control antibodies (all BD Pharmingen) for 35-40 min on ice at 4° C. Cells were washed, incubated with 7-AAD cell viability solution (eBioscience), and analyzed on a LSR-I (BD Biosciences). Acquired data were analyzed using FlowJo software (Tree Star).

Derivation and Culture of Human Adipose Stromal Cells (hASC).

hASCs were obtained by lipoaspiration after acquiring informed consent from patients, in accordance with Stanford University human IRB guidelines. Lipoaspiration procedures were performed using the VASER Lipo System (Sound Surgical Technologies). Participating patients (n=4, ages between 40-65 years) had no evidence or systemic disease at the time of operation. Specimens were collected and sterilized by sequential washes of serially dilute Betadine, followed by PBS. Adipose tissue was then digested with 0.075% (wt/vol) Type II collagenase in Hank's balanced salt solution at 37° C. in water bath with agitation for 30 min. Serum was added to inactivate collagenase and the stromal vascular fraction was pelleted, resuspended, and filtered through a 100-μm cell strainer. The collected cells were plated inside 15-cm dishes in maintenance medium consisting of Dulbecco's modified Eagle medium (DMEM) containing 10% FBS, Glutamax-I 4.5 g/L glucose, 110 mg/L sodium pyruvate, 50 U/mL penicillin, and 50 μg/mL streptomycin.

Reprogramming of hASCs to hiPSCs.

For lentivirus production, 293T cells (Invitrogen) were transfected with 12 μg of each lentiviral vectors (Oct4, Klf4, c-MYC, Sox2), plus 8 μg packaging plasmids, and 4 μg VSVG plasmids using Lipofectamine 2000 (Invitrogen) per the manufacturer's instructions. Forty-eight hours post-transfection, the supernatant was collected, filtered, mixed with PEG-it Virus Concentration Solution (Systems Biosciences) overnight, and viruses were precipitated the next day. Individual lentiviral plasmids were constructed for human Oct3/4, Klf4, Sox2 and c-MYC. cDNAs were amplified by PCR and subcloned into modified pLL3.7 plasmids under the CMV promoter. For hiPSC derivation, hASCs were reprogrammed on Matrigel-coated feeder-free surfaces. Cells were transduced twice with the four individual lentiviruses on days 0 and 2. At day 4, the medium was switched from hASC maintenance medium to mTeSR-1. Media was changed daily and ES-like colonies appeared as early as days 13-14. On days 19-20, colonies with ES-like morphologies that demonstrated positive immunostaining for TRA-1-60 expression were picked out and expanded in feeder-free conditions as described above.

Characterization of hiPSCs.

For immunofluorescense and Alkaline Phosphatase Staining, cells were fixed with 2% formaldehyde, permeabilized with 0.5% Triton X-100 for 10 min, and blocked with 5% BSA for 1 h. Cells were stained with the following primary antibodies: Oct314 (Santa Cruz Biotechnology), SSEA-3, SSEA-4, Tra-1-60 (all Chemicon), Nanog (Santa Cruz Biotechnology). Alkaline phosphatase (AP) staining was performed using the quantitative AP staining ES characterization kit (Chemicon) per manufacturer's instructions. For RT-PCR, total RNA and cDNA of each sample were prepared using the RNeasy Mini Plus Kit (Qiagen), respectively, following the manufacturer's instructions. PCR was performed with Pfu Ultra II polymerase (Stratagene). The primer sequences used for amplification of the pluripotency transcription factors are: (Oct4) 352F ACCCCTGGTGC-CGTGAA (SEQ ID NO:1), 541R GGCTGAATACCTTC-CCAAATA (SEQ ID NO:2). (Sox2) 890F CAGCGCATG-GACAGTTAC (SEQ ID NO:3), 1210R GGAGTGGGAGGAAGAGGT (SEQ ID NO:4). (Nanog) 433F AAAGGCAAACAACCCACT (SEQ ID NO:5), 702R GCTATTCTTCGGCCAGTT (SEQ ID NO:6).

Microarray Hybridization and Data Acquisition for hiPSC, and hASCs.

Total RNA was isolated using Qiagen RNeasy (Qiagen, Valencia, Calif., USA) from cell cultures of hASC-derived iPSCs (n=4), H7 hESCs (n=2), and hASCs (n=2), for a total of eight unique samples. Using Agilent Low RNA Input Fluorescent Linear Amplification Kits, cDNA was reverse transcribed from each sample, as well as a pooled reference control, and cRNA was then transcribed and fluorescently labeled with Cy5/Cy3. cRNA was purified using an RNeasy kit (Qiagen, Valencia, Calif., USA). 825 ng of Cy3- and Cy5-labeled and amplified cRNA was hybridized to Agilent 4×44K whole human genome microarrays (G4112F) and processed according to the manufacturer's instructions. The array was scanned using Agilent G2505B DNA microarray scanner. The image files were extracted using Agilent Feature Extraction software version 9.5.1 applying LOWESS background subtraction and dye-normalization. The data were analyzed using GeneSpring GX 10.0 (Agilent Technologies, Santa Clara, Calif.) to identify genes which had statistically significantly changed expression between groups using one-way ANOVA. Genes were considered significantly differentially regulated with P-value<0.05 and fold change z 2.0. For hierarchical clustering, we used Pearson correlation for similarity measure and average linkage clustering. In the heatmap, we averaged the intensity values for the H7 hESC and hASC arrays.

Derivation, culture, and reprogramming of mouse neural stem cells (mNSC) to mouse iPSCs (miPSC). mNSCs were isolated as previously described. Briefly, mouse brain was explanted from FVB mice and minced until a single cell suspension was attained. The isolated cells were cultured in NSC medium[4] for 6-8 days until neurospheres were evident and the NSCs had outgrown the attached neurospheres. The NSCs were reprogrammed to miPSCs by lentiviral transduction as described, with minor modifications. Briefly, NSCs were transduced twice with only Oct4 containing lentiviruses on days 0 and 2. At day 4-5, the medium was switched from NSC medium to mESC medium as detailed above.

Apoptosis Assay.

Effect of costimulatory blockade on hESC, viability was evaluated via flow cytometry using fluorescently-conjugated Annexin V (BD Pharmingen). $5 \times 10^5$ hESCs were incubated with either no COSTIM, low COSTIM (5 μg CTLA4-Ig, 5 μg anti-LFA-1, 5 μg anti-CD40L), or high COSTIM (500 μg CTLA4-Ig, 500 μg anti-LFA-1, 500 μg anti-CD40L) exposure. hESCs were then washed and incubated in Annexin V binding buffer with Annexin V at a 1:20 dilution for 15 minutes at room temperature. The cells were then washed, resuspended in Annexin V binding buffer, and analyzed by flow cytometry immediately. Annexin V staining was done in conjunction with the vital dye 7-amino-actinomycin D (7-AAD) to differentiate early apoptosis (Annexin V+ 7-AAD−) from late apoptosis/necrosis (Annexin V+ 7-AAD+).

Mixed Lymphocyte Reaction.

Splenocytes were harvested from either FVB/N (stimulator) or C57BL/6 (responder) mice (Jackson Laboratories)

and processed in PBS supplemented with 2% FCS (Invitrogen), n=4 mice per group. After ACK red blood cell lysis of single cell suspensions, cells were placed in cRPMI media with 10% FCS, 2 mM L-glutamine, 100 U/ml penicillin, 100 µg/ml streptomycin (all from Invitrogen), and 5 µg/mL 2-mercaptoethanol (Sigma-Aldrich). Responder cells were labeled with 5 µM CFSE from CellTrace™ CFSE Cell Proliferation Kit (Invitrogen). Mixed lymphocyte reaction was conducted by placing $8 \times 10^5$ FVB/N splenocytes, which had been irradiated with 30 Gy, into each well of a 96-well plate together with $2 \times 10^5$ CFSE-labeled C57BL/6 cells in a total volume of 250 µL cRPMI. Proliferation of C57BL/6 responders was assessed by FACS analysis after 5 days of incubation with or without 50 µg CTLA4-Ig, 50 µg anti-LFA-1, 50 µg anti-CD40L. Assays were performed in triplicate. Shown is a representative, trial chosen from three independent trials demonstrating similar results.

RNA Collection and Microarray Analysis of Responder Splenocytes.

Following the MLR, responder splenocytes were washed, resuspended in FACS buffer, and incubated with mouse-anti-human $CD4^+$ and $CD8^+$ antibodies (BD Biosciences) for 30 min at 4° C. Responder T-cell subsets were then isolated by FACS on a Vantage SE cell sorter (Becton Dickinson Immunocytometry Systems) analyzing for cells which were double positive for FITC (CFSE) and either CD4 or CD8. Sorted cells were collected and $3 \times 10^5$ cells were counted using a hemocytometer, and total RNA was immediately extracted using the RNeasy micro kit (Qiagen) per manufacturer's instructions. The RNA samples were hybridized to the Affymetrix Mouse 430 2.0 chips, and the expression signals were scanned on an Affymetrix GeneChip Scanner. All data sets were analyzed using GeneSpring GX 10.0 software (Agilent Technologies). Gene-level signal estimates were derived from the CEL files. Summarization of gene expression data was performed by implementing the robust multichip averaging algorithm, with subsequent baseline normalization of the log-summarized values for each probe set to that of the median log summarized value for the same probe set in the control group. Expression data were then filtered to remove probe sets for which the signal intensities for all the treatment groups were in the lowest 20 percentile of all intensity values. The data were then subjected to Student's t-test, incorporating the Benjamini-Hochberg FDR multiple testing correction, with a significance level of P-value<0.05 to get the differentially expressed genes between two groups. Probe sets were further filtered on the basis of a fold-change cut off of 2.0. Hierarchical clustering was performed by complete linkage and uncentered correlation using the open source clustering software Cluster 3.0. Results were visualized using Java TreeView. In order to perform functional annotation of the differentially expressed genes between COSTIM treated and untreated groups, we used Ingenuity Pathway Analysis (IPA) software. This software assigns biological functions to genes using the Ingenuity Pathways Knowledge Base (Ingenuity Systems, Inc). Two independent experiments were conducted, requiring a total of 8 chips.

Statistical Analysis.

Data were processed using Prism 5.0 software. Values are reported as mean±SEM. Comparisons between groups were done by independent sample t tests or ANOVA with LSD post-hoc or Bonferroni post-tests, where appropriate. Differences were considered significant for P<0.05. Statistical analysis was performed using SPSS statistical software for Mac (SPSS).

Example 2

Allogeneic and Xenogeneic Transplantation of iPSCs and Progenitor Cells Results in Immune Rejection which can be Prevented by Costimulatory Blockade For regenerative medicine purposes, an alternative source of pluripotent cells is human induced pluripotent stem cells (hiPSC). hiPSCs can be generated by delivering transcription factors to reprogram somatic cells towards a state of pluripotency. To assess the immunogenic properties of hiPSCs and the efficacy of costimulatory blockade to induce long-term engraftment of hiPSCs, we created four hiPSC lines from human adipose stem cells (hASC) isolated from four different patients. These hiPSC colonies stained positive for the pluripotency markers, alkaline phosphatase (AP), Nanog, SSEA-3, SSEA-4, and Oct4. Compared to undifferentiated hESCs, the hiPSCs demonstrated similar surface expression levels of pluripotency marker SSEA-4, lack of MHC-II, and slightly higher levels of MHC-I. We performed microarray gene expression analyses which demonstrated that the four hiPSC lines are similar to H7 hESCs (Wicell) and distinct from hASCs (FIG. 5A). The pluripotency of hiPSCs was examined through the formation of embryoid bodies (EBs). hiPSC-EBs expressed multiple markers corresponding to each of the three embryonic germ layers (FIG. 5B).

The hiPSC-EBs demonstrated the capacity for multilineage differentiation as we were able to derive neurons, endothelial cells, and beating cardiomyocytes (FIG. 5B, 5C). Upon transplantation into immunocompetent mice, hiPSC survival was significantly limited in untreated compared with costimulatory blockade treated mice as the BLI signal decreased to background levels in untreated animals by 7 days post-transplantation, whereas engraftment with steadily increasing BLI signal and teratoma formation were observed in costimulatory blockade treated animals (P<0.01, FIGS. 4A, 5D).

Figure 4:
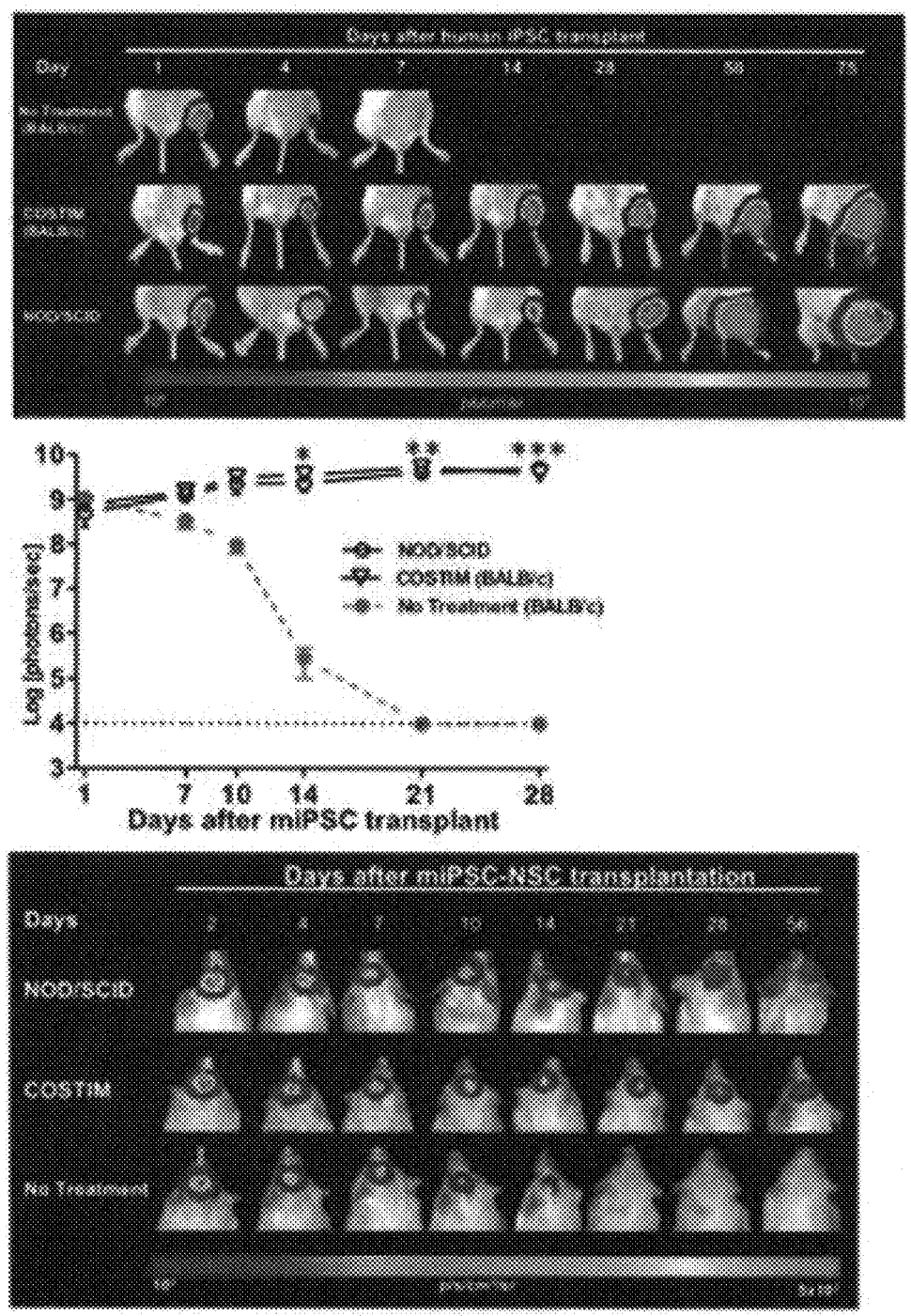
FIG. 4. Leukocyte costimulatory molecule blockade permits xenogeneic and allogeneic engraftment of hiPSC, miPSC, and differentiated miPSC-derivatives. Filled histograms represent isotype control antibodies. BLI and bioluminescence photon intensities representing the survival of (a) hiPSCs and (b) miPSCs transplanted into the gastrocnemius muscle of immunodeficient (NOD/SCID) and immunocompetent mice receiving costimulatory blockade (COSTIM) or no treatment, n=3-5 per group, *P<0.05, *P<0.01, ***P<0.001. (c) In vitro differentiated miPSC-NSCs transplanted into the subcortical area of the brain in immunodeficient (NOD/SCID) and immunocompetent mice. n=3-4 per group.

To assess efficacy of costimulatory blockade in an allogeneic transplant model, we generated miPSCs from FVB (H-$2k_q$) mice and followed survival in BALB/c (H-2 $k_d$) mice by in vivo BLI. In the absence of immunosuppression, transplanted miPSC survival was significantly limited to 14 to 21 days post transplantation. However, when allogeneic mice were treated with costimulatory blockade, prolonged engraftment with steadily increasing BLI signal and teratoma formation were observed in all animals (FIGS. 4B, 5E).

Similar to ESC-based therapy, iPSC-based therapy will likely utilize a differentiated rather than undifferentiated cell population. Hence we generated miPSC-derived neural stem cells (miPSCNSC) (FIG. 5C) to investigate the survival of this cell population in untreated and costimulatory blockade treated allogeneic recipients. Survival of miPSC-NSCs was significantly limited in untreated compared to costimulatory blockade treated mice (P<0.01, FIG. 4C). At day 14 following transplantation, the BLI signal in the untreated group was 24.7±6.8% of the initial BLI intensity, compared to 60.9±6.5% in the costimulatory blockade treated group (P<0.01). By day 21, the BLI signal in the untreated group had diminished to background intensity whereas the BLI signal was 51.1±5.3% of the initial BLI intensity in the costimulatory blockade treated group (P<0.001).

Costimulatory blockade inhibits allogeneic leukocyte proliferation with limited systemic toxicity. To evaluate the toxicity of the costimulatory blockade agents on the host, we compared hematologic, renal, hepatic, and metabolic parameters between costimulatory blockade and untreated mice. For all parameters assayed, costimulatory blockade mice demonstrated similar laboratory values as untreated mice. The low toxicity of costimulatory blockade immunosuppression highlights another advantage of costimulatory blockade over traditional immunosuppressive approaches (e.g., TAC and SIR). Another advantage is that costimulatory blockade requires only a short period of administration. However, if costimulatory blockade diminishes the ability of the host to mount a robust immune response to future antigens, then the potential for clinical translation of this approach would be severely decreased.

To address the ability of costimulatory blockade treated hosts to reject third party antigens, hESCs were injected into immunocompetent mice which had previously accepted miPSC-NSC grafts. The transplanted hESCs were rejected, indicating that despite previous costimulatory blockade treatment, the mice were fully capable of rejecting third party antigens.

To determine the contribution of T regulatory (Treg) cells towards the costimulatory blockade induced survival of hESCs, we compared the absolute number of CD4+FoxP3+ T cells in costimulatory blockade and untreated mice 21 days after hESC transplantation. Relative to untreated controls, costimulatory blockade significantly decreased the total number of CD4+FoxP3+ T cells (P=0.002), as well as the percent of CD4+ T cells that were CD4+FoxP3+ cells (P=0.006)). To assess the immunosuppressive ability of the Treg cells which develop in costimulatory blockade treated mice, MLRs were performed as described above, with or without the inclusion of CD4+CD25$_{hi}$ T cells. The inclusion of CD4+CD25$_{hi}$ T cells significantly mitigated the proliferation of CD8+ T cells (P=0.0005). However, the CD4+CD25$_{hi}$ T cells isolated from costimulatory blockade mice did not possess a significantly different immunosuppressive potency than CD4+CD25$_{hi}$ T cells isolated from untreated mice (P=NS).

What is claimed is:

1. A method for the transplantation of mammalian cells derived from donor stem cells, the method comprising:
   introducing said mammalian cells derived from donor stem cells differentiated in vitro, to a recipient; and
   providing said recipient with a cocktail comprising at least two leukocyte costimulatory molecule blocking agents selected from anti-LFA-1, anti-CD40L, and CTLA4-Ig, administered for less than 2 weeks, in the absence of a small molecule general immunosuppressant, to allow for long term engraftment of the mammalian cells derived from donor stem cells.

2. The method according to claim 1, wherein said mammalian cells derived from donor stem cells are differentiated cells.

3. The method of claim 2, wherein the differentiated cells are neural progenitor cells.

4. The method according to claim 1, wherein said cells are derived from embryonic stem cells.

5. The method according to claim 1, wherein said cells are derived from induced pluripotent stem cells.

6. The method of claim 1, wherein said cocktail comprises three leukocyte costimulatory molecule blocking agents.

7. The method of claim 1, wherein the cocktail of leukocyte costimulatory molecule blocking agents is administered for less than 1 week.

* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Synthetic primer

<400> SEQUENCE: 1
acccctggtg ccgtgaa                                                  17

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ggctgaatac cttcccaaat a                                             21

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
cagcgcatgg acagttac                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
ggagtgggag gaagaggt                                                 18

<210> SEQ ID NO 5
<211> LENGTH: 18
<212> TYPE: DNA
```

```
<213> ORGANISM: Artificial Sequence
<220> FEATURE:
<223> OTHER INFORMATION: Synthetic primer

<400> SEQUENCE: 5
aaaggcaaac aacccact                                                  18

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
gctattcttc ggccagtt                                                  18
```